(12) United States Patent
Yeh

(10) Patent No.: US 10,556,065 B2
(45) Date of Patent: Feb. 11, 2020

(54) SYRINGE

(71) Applicant: CC Biotechnology Corporation, Tainan (TW)

(72) Inventor: Chin-Min Yeh, Tainan (TW)

(73) Assignee: CC Biotechnology Corporation, Tainan (TW)

( * ) Notice: Subject to any disclaimer, the term of this patent is extended or adjusted under 35 U.S.C. 154(b) by 313 days.

(21) Appl. No.: 15/561,575

(22) PCT Filed: Feb. 4, 2016

(86) PCT No.: PCT/CN2016/073530
§ 371 (c)(1),
(2) Date: Sep. 26, 2017

(87) PCT Pub. No.: WO2016/155418
PCT Pub. Date: Oct. 6, 2016

(65) Prior Publication Data
US 2018/0078709 A1 Mar. 22, 2018

(30) Foreign Application Priority Data
Apr. 1, 2015 (CN) .......................... 2015 1 01499806

(51) Int. Cl.
*A61M 5/315* (2006.01)
*A61M 5/24* (2006.01)
*A61M 5/32* (2006.01)

(52) U.S. Cl.
CPC .......... *A61M 5/31538* (2013.01); *A61M 5/24* (2013.01); *A61M 5/31581* (2013.01); *A61M 5/3202* (2013.01)

(58) Field of Classification Search
CPC .......... A61M 5/31538; A61M 5/31536; A61M 5/31535; A61M 5/31533; A61M 5/315;
(Continued)

(56) References Cited

U.S. PATENT DOCUMENTS 2,752,918 A * 7/1956 Uytenbogaar ...... A61M 5/2033
604/136
3,780,734 A * 12/1973 Wulff .................... A61M 5/178
604/197
(Continued)

FOREIGN PATENT DOCUMENTS

CN 201631814 U 11/2010
CN 203090111 U 7/2013
(Continued)

*Primary Examiner* — Nathan R Price
*Assistant Examiner* — Mark A Igel
(74) *Attorney, Agent, or Firm* — Alan D. Kamrath; Karin L. Williams; Mayer & Williams PC

(57) ABSTRACT

An injection pen comprises a circularly pushing device (1) and a vial housing (2), and is used to combine a medication vial (3) with a needle (4). The circularly pushing device (1) comprises a jointing member (10), a spiral sleeve (20), a spiral duct (30), a spirally-pushing tube (40), a threaded-connection shrink-ring (50), a propelling lever (60), a one-way ratchet ring (70), and an injection operation member (80). During the injection, the one-way ratchet ring (70) on a push rod (81) is jointed with a one-way ratchet groove portion (46) of the spirally-pushing tube (40) so as to restrain the rotation directions of the push rod (81) and the spirally-pushing tube (40); the propelling lever (60) cannot be rotated due to the limit of the jointing member (10).

16 Claims, 13 Drawing Sheets

(58) Field of Classification Search
CPC ........ A61M 5/178; A61M 5/502; A61M 5/20; A61M 5/24; A61M 5/3202; A61M 5/50; A61M 5/5013; A61M 5/32; A61M 5/31526; A61M 2005/2073
See application file for complete search history.

(56) References Cited

U.S. PATENT DOCUMENTS

| | | | | |
|---|---|---|---|---|
| 3,890,971 | A * | 6/1975 | Leeson | A61M 5/24 604/110 |
| 4,367,738 | A * | 1/1983 | Legendre | A61M 5/5013 604/110 |
| 4,413,760 | A * | 11/1983 | Paton | A61M 5/3158 222/309 |
| 4,592,745 | A * | 6/1986 | Rex | A61M 5/24 604/152 |
| 5,545,147 | A * | 8/1996 | Harris | A61M 5/31551 604/209 |
| 5,611,783 | A * | 3/1997 | Mikkelsen | A61M 5/24 604/208 |
| 5,984,900 | A * | 11/1999 | Mikkelsen | A61M 5/24 604/135 |
| 6,004,297 | A * | 12/1999 | Steenfeldt-Jensen | A61M 5/31551 604/207 |
| 7,291,132 | B2 | 11/2007 | DeRuntz et al. | |
| 7,427,275 | B2 | 9/2008 | DeRuntz et al. | |
| 7,749,200 | B2 * | 7/2010 | Graf | A61M 5/31551 604/187 |
| 8,444,606 | B2 * | 5/2013 | Radmer | A61M 5/31528 604/211 |
| 8,647,309 | B2 * | 2/2014 | Harms | A61M 5/24 604/207 |
| 9,205,196 | B2 | 12/2015 | Harms et al. | |
| 9,623,181 | B2 * | 4/2017 | Brereton | A61M 5/2033 |
| 9,744,311 | B2 * | 8/2017 | Streit | A61M 5/20 |
| 2006/0206057 | A1 * | 9/2006 | DeRuntz | A61M 5/31551 604/224 |
| 2006/0224124 | A1 * | 10/2006 | Scherer | A61M 5/2033 604/220 |
| 2007/0073232 | A1 * | 3/2007 | Pickhard | A61M 5/2033 604/134 |
| 2008/0108953 | A1 * | 5/2008 | Moser | A61M 5/31553 604/224 |
| 2008/0208123 | A1 * | 8/2008 | Hommann | A61M 5/2033 604/123 |
| 2008/0262438 | A1 * | 10/2008 | Bollenbach | A61M 5/2033 604/207 |
| 2010/0137798 | A1 * | 6/2010 | Streit | A61M 5/2033 604/110 |
| 2010/0268171 | A1 * | 10/2010 | Moller | A61M 5/31551 604/246 |
| 2012/0209192 | A1 * | 8/2012 | Alexandersson | A61M 5/2033 604/135 |
| 2012/0283655 | A1 * | 11/2012 | Plumptre | A61M 5/31543 604/211 |
| 2014/0249482 | A1 * | 9/2014 | Wieselblad | A61M 5/31551 604/211 |
| 2016/0008542 | A1 * | 1/2016 | Hirschel | A61M 5/2033 604/137 |
| 2016/0129196 | A1 * | 5/2016 | Hirschel | A61M 5/31541 604/211 |
| 2017/0007773 | A1 * | 1/2017 | Yeh | A61M 5/31555 |
| 2018/0078709 | A1 * | 3/2018 | Yeh | A61M 5/24 |
| 2018/0085536 | A1 * | 3/2018 | Yeh | A61M 5/31501 |

FOREIGN PATENT DOCUMENTS

| | | |
|---|---|---|
| TW | M447781 U | 3/2013 |
| TW | M462121 U | 9/2013 |
| TW | M483803 U | 8/2014 |
| WO | WO2005018721 A1 | 3/2005 |

\* cited by examiner

SYRINGE

BACKGROUND OF THE INVENTION

1. Field of the Invention

The present invention relates to a syringe, especially to a syringe that safely controls the injection dose and is labor-saving in operation.

2. Description of Related Art

In order to achieve multiple purposes such as dose metering, injection time counting, and repeatable use, the conventional syringes include two kinds: a dose metering syringe and a frequency measuring syringe. The structure of the conventional dose metering syringe mainly includes a driving device assembled by multiple driving components mounted in a barrel and connected with a piston rod. A vial is assembled in the barrel. A needle is mounted on a front end of the barrel and is connected with the vial for injection. When the syringe is in an injecting process, the needle is pierced into the skin or the veins of a human body, and the driving device is driven by pushing the piston rod to inject the medication. The dose of the injection can be controlled by the driving device and the movement of the piston rod to achieve the purpose of dose-metering.

However, the conventional dose metering syringe still has an issue of laboriousness. To solve the laboriousness issue, the conventional dose metering syringe has a structure that comprises a large pitch travel structure and a small pitch travel structure, such that the pushing force provided by a user can be effectively transformed to a rotating force. Accordingly, the operation of the conventional syringe is labor-saving.

However, an injection rod may be pulled backward during the operation of the conventional dose metering syringe, so the safety of use of the conventional syringe should be improved.

To overcome the shortcomings of the conventional dose metering syringe, the present invention provides a syringe to mitigate or obviate the aforementioned problems.

SUMMARY OF THE INVENTION

The main objective of the present invention is to provide a syringe to keep an injection rod of the syringe from being pulled backward.

The syringe has an injection assembly and a vial housing. The vial housing is adapted to connect a vial with the injection assembly. The injection assembly has a connecting element, a sleeve, a guiding tube, a screwing tube, a screwing collar, a pushing rod, a unidirectional ratchet collar, and an injection device. The connecting element has an inner flange and multiple unidirectional teeth. The inner flange is formed in the connecting element and has a guiding hole defined through the inner flange. The unidirectional teeth are formed on an inner surface of the connecting element. The sleeve is connected with a rear end of the connecting element and has an inner front segment, an inner rear segment, a recycling groove, and a resilient limiting tab. The inner rear segment communicates with the inner front segment. The recycling groove is defined in an inner surface of the inner rear segment and is composed of a spiral groove and a straight groove. The resilient limiting tab is formed on a rear end of the sleeve. The guiding tube is mounted in the inner front segment of the sleeve and has a tubular body, a front tube segment, and a shoulder. The tubular body has a spiral guiding groove defined in an inner surface of the tubular body. The front tube segment extends out of the inner front segment, extends into the rear segment of the connecting element, and has multiple limiting ratchet tabs fog iced on an outer surface of the front tube segment and engaged with the unidirectional teeth. The shoulder is formed between the tubular body and the front tube segment. The screwing tube is mounted in the sleeve and the guiding tube, extends out of the rear ends of the sleeve and the guiding tube, and has an axial hole, a guiding block, a guiding protrusion, a releasing channel, multiple annular grooves, and multiple unidirectional ratchet teeth. The axial hole is defined axially through the screwing tube. The guiding block is formed on a front end of the screwing tube and is mounted in the guiding groove. The guiding protrusion is formed on an outer surface at a middle portion of the screwing tube and is moveable in the recycling groove composed of the spiral groove and the straight groove. The releasing channel is longitudinally defined in an outer surface of the screwing tube and is diametrically opposite to the guiding protrusion. The annular grooves are defined around the outer surface of the screwing tube and are arranged longitudinally at evenly spaced intervals. The limiting tab on the sleeve is capable of being shifted between the releasing channel and the annular grooves. The unidirectional ratchet teeth are formed on an inner surface of the axial hole. The screwing collar is mounted in the front tube segment of the guiding tube and has a threaded hole. The pushing rod is mounted in the screwing tube and has a rod body and a dose controlling segment. The rod body has a non-circular cross section corresponding to a shape of the guiding hole of the connecting element. The dose controlling segment is formed on a front segment of the rod body and is provided with a thread that has a pitch smaller than a pitch of the spiral guiding groove, is screwed with the threaded hole in the screwing collar, and extends through the guiding hole in the connecting element. The unidirectional ratchet collar is mounted in the screwing tube, is located behind the pushing rod, and has a collar body and multiple unidirectional ratchet tabs formed on and protruding from an outer surface of the collar body and engaged with the unidirectional ratchet teeth of the screwing tube. The injection device has an injection rod and an end cap. The injection rod moveably extends into the sleeve and the screwing tube, through the ratchet collar, and into the axial hole in the pushing rod. The end cap is mounted on a rear end of the injection rod and is connected rotatably with the rear end of the screwing tube. The vial housing is connected with the injection assembly.

Wherein, the front tube segment of the guiding tube has an outer diameter smaller than an outer diameter of the tubular body. The guiding tube has a tube hole defined in the guiding tube. The spiral guiding groove is formed in an inner surface of the tube hole. Multiple limiting ratchet tabs are formed on an outer surface of the front tube segment. A front tube hole is defined in the front tube segment. A central hole is defined in the guiding tube at a position corresponding to the shoulder, and the front tube hole communicates with the tube hole via the central hole. Multiple holding notches are defined in an inner surface of the front tube hole. The screwing collar has multiple holding blocks formed on an outer surface of the screwing collar and engaged respectively with the holding notches of the guiding tube.

Wherein, the rod body of the pushing rod has multiple cavities defined in an inner surface of the axial hole at the rear end of the rod body. The ratchet collar has multiple collar hooks formed on a front end of the ratchet collar and engaged respectively with the cavities in the axial hole of the rod body of the pushing rod. The screwing tube further has a pivotal connection portion formed on the rear end of the screwing tube and provided with hooks. The injection rod has a combining segment provided with a flange and formed on the rear end of the pushing rod. The end cap comprises a cap body and a lid. The cap body has a combining hole. The lid is mounted on a rear end of the cap body. The combining segment of the injection rod and the pivotal connection portion of the screwing tube are mounted through the combining hole in the cap body.

Wherein, the pushing rod has multiple engaging holes and a rod tube. The engaging holes are radially defined in a front end of the dose controlling segment and communicate with the axial hole of the pushing rod. The rod tube is mounted securely on the front end of the rod body of the pushing rod and has an abutting segment and a holding segment. The holding segment is connected with the abutting segment, is mounted around a front end of the rod body of the pushing rod, and has multiple hooks formed in the holding segment and engaged respectively with the engaging holes in the rod body of the pushing rod.

Wherein, the front tube segment of the guiding tube has an outer diameter smaller than an outer diameter of the tubular body of the guiding tube to define the shoulder between the tubular body and the front tube segment. The guiding tube has a tube hole defined in the guiding tube. The spiral guiding groove is formed in an inner surface of the tube hole. Multiple limiting ratchet tabs are formed on an outer surface of the front tube segment. A front tube hole is defined in the front tube segment. A central hole is defined in the guiding tube at a position corresponding to the shoulder, and the front tube hole communicates with the tube hole via the central hole. Multiple holding notches are defined in an inner surface of the front tube hole. The screwing collar has multiple holding blocks formed on an outer surface of the screwing collar and engaged respectively with the holding notches of the guiding tube. The rod body of the pushing rod has multiple cavities defined in an inner surface of the axial hole at the rear end of the rod body. The ratchet collar has multiple collar hooks formed on a front end of the ratchet collar and engaged respectively with the cavities in the axial hole of the rod body of the pushing rod. The screwing tube further has a pivotal connection portion formed on the rear end of the screwing tube and provided with hooks. The injection rod has a combining segment provided with a flange and formed on the rear end of the pushing rod. The end cap comprises a cap body and a lid. The cap body has a combining hole. The lid is mounted on a rear end of the cap body. The combining segment of the injection rod and the pivotal connection portion of the screwing tube are mounted through the combining hole in the cap body. The pushing rod has multiple engaging holes and a rod tube. The engaging holes are radially defined in a front end of the dose controlling segment and communicate with the axial hole of the pushing rod. The rod tube is mounted securely on the front end of the rod body of the pushing rod and has an abutting segment and a holding segment connected with the abutting segment, mounted around a front end of the rod body of the pushing rod, and having multiple hooks formed in the holding segment and engaged respectively with the engaging holes in the rod body of the pushing rod.

Wherein, the injection rod has multiple engaging faces formed on a front segment of the injection rod. The guiding tube has a locking tube in the guiding tube. The pushing rod has multiple through holes and multiple resilient hooks. The through holes are defined radially in the pushing rod at a position adjacent to the dose controlling segment. The resilient hooks are formed on the pushing rod, extend respectively into the through holes, and are selectively pushed by the locking tube to abut respectively against the engaging faces on the injection rod.

Wherein, the syringe further comprises a syringe housing and a syringe cap. The syringe housing is a hollow barrel, is mounted around the sleeve, and is connected with the rear end of the connecting element. The syringe cap is mounted detachably around the vial housing. The combining segment of the injection rod and the pivotal connection portion of the screwing tube extend out of a rear end of the syringe housing and are combined with the end cap.

Wherein, the connecting element comprises a middle segment, a front segment, a rear segment, and a connecting segment. The front segment and the rear segment are formed respectively at two ends of the middle segment. The connecting segment is formed on and protrudes from the middle segment, extends toward the rear segment, and is disposed around the rear segment. The rear segment has an outer diameter smaller than an outer diameter of the front segment. Multiple first hooks are formed on the front segment. Multiple protrusions are formed on and protrude from an outer surface of the connecting segment, and each protrusion has an inclined surface. Multiple second hooks are formed on a rear end of the middle segment and extend into a space defined between the connecting segment and the rear segment. Two alignment notches are defined in a rear end of the connecting segment. The vial housing has a connection segment formed on a rear end of the vial housing, mounted around the front segment of the connecting element, and having multiple hook holes engaged respectively with the first hooks on the front segment of the connecting element. The syringe housing has a front end mounted around the connecting segment of the connecting element and multiple cavities defined in the front end of the syringe housing and engaged respectively with the protrusions on the connecting segment of the connecting element. The sleeve is inserted into the space defined between the rear segment and the connecting segment of the connecting element and has multiple engaging holes and two alignment protrusions. The engaging holes are defined in the connection segment of the sleeve and are engaged respectively with the second hooks of the connecting element. The alignment protrusions are inserted respectively into the alignment notches in the connecting segment of the connecting element.

Wherein, the injection rod has multiple engaging faces formed on a front segment of the injection rod. The guiding tube has a locking tube in the guiding tube. The pushing rod has multiple through holes and multiple resilient hooks. The through holes are defined radially in the pushing rod at a position adjacent to the dose controlling segment. The resilient hooks are formed on the pushing rod, extend respectively into the through holes, and are selectively pushed by the locking tube to abut respectively against the engaging faces on the injection rod.

With aforementioned features, since the pitch of the spiral guiding groove is larger than that of the thread on the pushing rod, the pushing force applied to the injection device can be transformed to a rotating force efficiently. Accordingly, the rotating force along the large pitch along the spiral guiding groove can be effectively transmitted to the small pitch along the thread, such that the dose controlling effect is provided and the syringe is labor-saving in operation. In addition, the rotation direction of the injection rod and the screwing tube is limited due to the engagement between unidirectional ratchet tabs on the ratchet collar and the unidirectional ratchet teeth on the screwing tube. The pushing rod is kept from being rotated due to the non-circular guiding hole in the connecting element. With a guiding protrusion held in a straight groove, the screwing tube can only be moved forward with the injection device. The screwing tube is kept from being moved backward again because of the arrangement of a spiral groove and the guiding protrusion of the screwing tube until the guiding block on the screwing tube moves along the spiral guiding groove in the guiding tube in a complete pitch. Accordingly, a dose controlling effect is provided and the safety of use of the syringe is improved.

When the medication in the vial is completely injected, the pushing rod is moved to a position where the resilient hooks are pushed by the locking tube in the guiding tube, and the resilient hooks are bent and extend into the pushing rod to abut against the engaging faces on the injection rod. Accordingly, the injection device can be prevented from being pulled backward and is locked, so the safety of use of the syringe can be improved.

Other objects, advantages and novel features of the invention will become more apparent from the following detailed description when taken in conjunction with the accompanying drawings.

DETAILED DESCRIPTION OF PREFERRED EMBODIMENT

Figure 1:
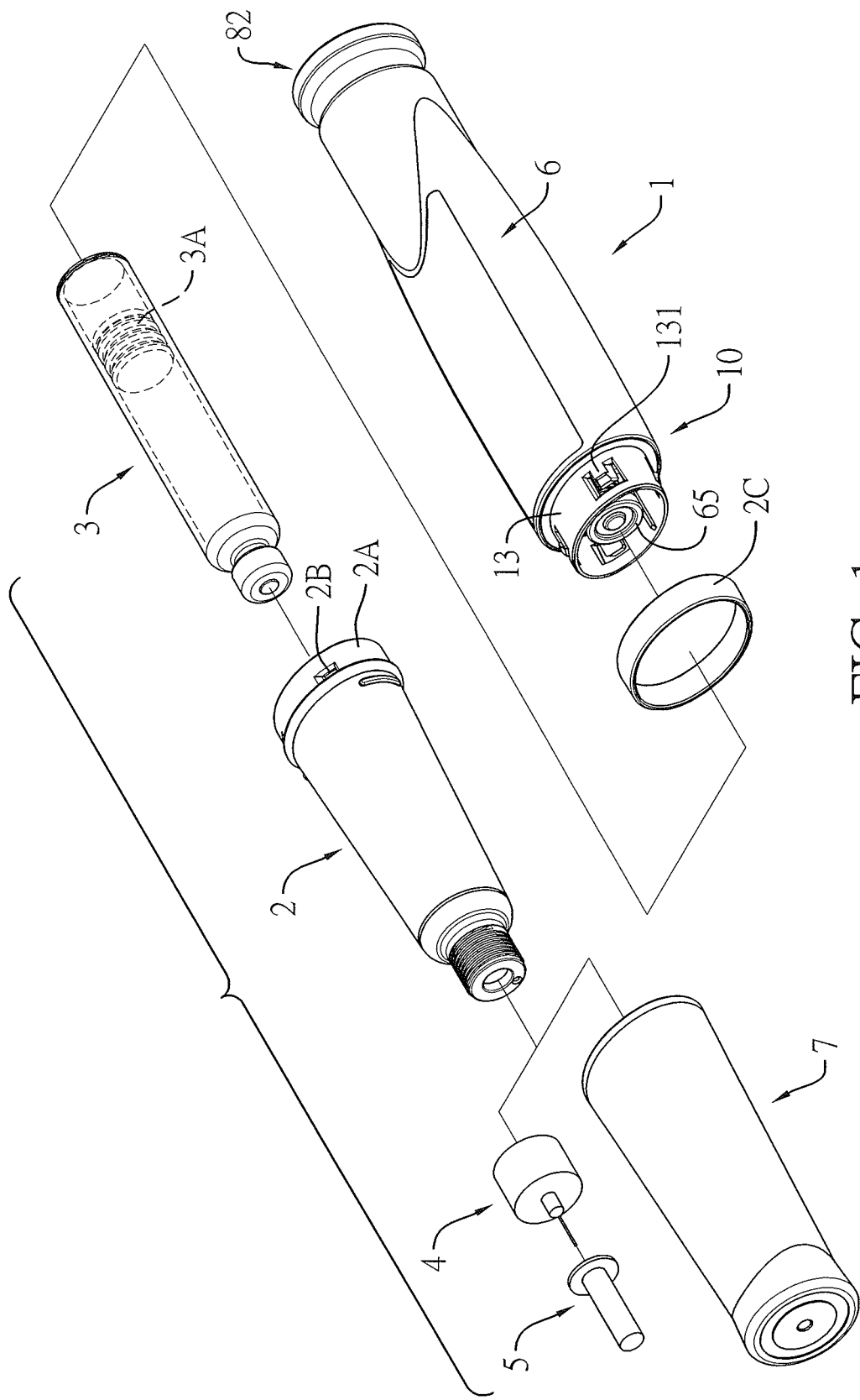
FIG. 1 is an exploded perspective view of a syringe in accordance with the present invention.

With the reference to FIG. 1, a syringe in accordance with the present invention can be combined with a vial 3, a needle 4, and a needle cap 5 and comprises an injection assembly 1 and a vial housing 2. In addition, the syringe may further comprise a syringe housing 6 and a syringe cap 7.

Figure 2:
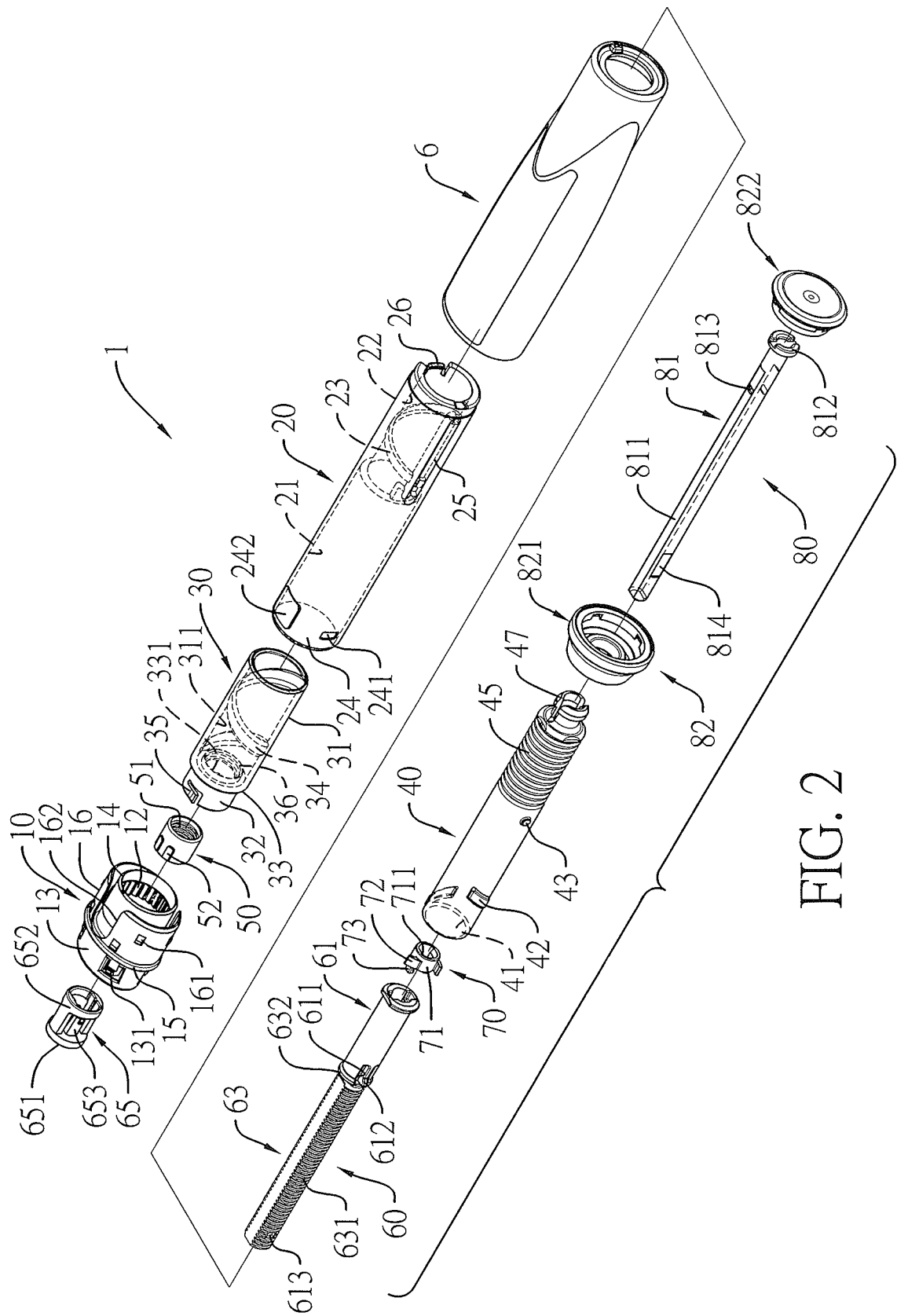
FIG. 2 is another exploded perspective view of the syringe in FIG. 1.
Figure 3:
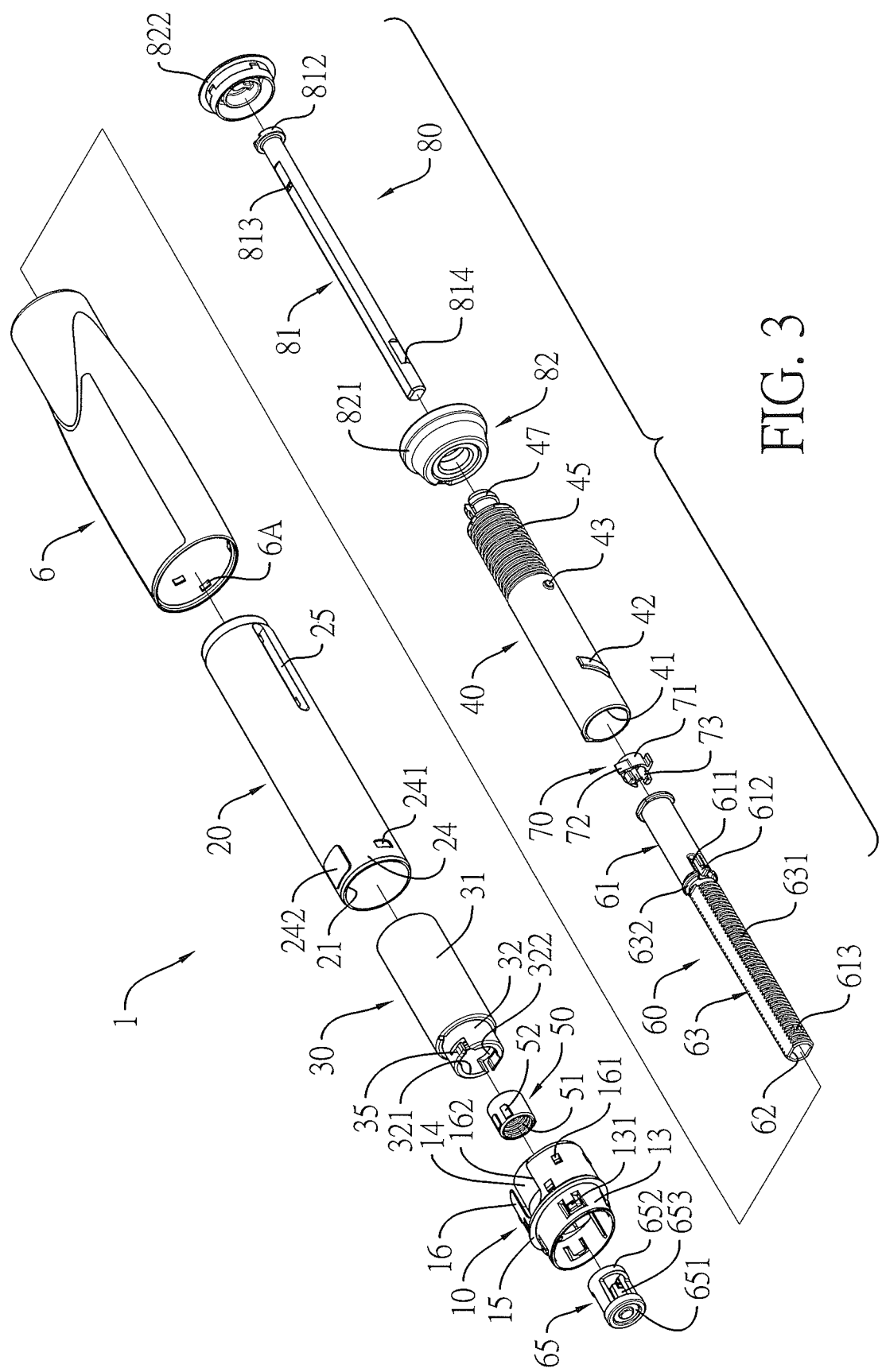
FIG. 3 is a further another exploded perspective view of the syringe in FIG. 1.

With reference to FIGS. 1 to 3, the injection assembly 1 includes a connecting element 10, a sleeve 20, a guiding tube 30, a screwing tube 40, a screwing collar 50, a pushing rod 60, a unidirectional ratchet collar 70, and an injection device 80.

With reference to FIGS. 2 to 6, the connecting element 10 comprises an inner flange 11 and multiple unidirectional teeth 12. The inner flange 11 is annularly formed on and protrudes from an inner surface of the connecting element 10. The guiding hole 111 is defined through the inner flange 11 and is a non-circular hole having two flat faces, such as a polygonal hole or a hole having two flat faces diametrically opposite each other. In the present embodiment, the connecting element 10 comprises a front segment 13, a rear segment 14, a middle segment 15, and a connecting segment 16. The front segment 13 and the rear segment 14 are formed respectively at two ends of the middle segment 15. The connecting segment 16 is formed on and protrudes from the middle segment 16, extends toward the rear segment 14, and is disposed around the rear segment 14. The front segment 13 is applied to be connected with a rear end of the vial housing 2, and the vial 3 can extend into the rear segment 14 via the front segment 13. The inner flange 11 and the unidirectional teeth 12 are formed on the inner surface of the rear segment 14.

In addition, multiple first hooks 131 are formed on the front segment 13 to engage with the vial housing 2. Multiple second hooks 141 are formed on a rear end of the middle segment 15 and extend into the space defined between the connecting segment 16 and the rear segment 14. Multiple protrusions 161 are formed on and protrude from an outer surface of the connecting segment 16, and each protrusion 161 has an inclined surface. Two alignment notches 162 are defined in a rear end of the connecting segment 16.

The sleeve 20 has a front end connected with a rear end of the guiding element 10. The sleeve 20 has an axial hole defined axially through the sleeve and composed of an inner front segment 21 and an inner rear segment 22 communicating with the inner front segment 21. The inner front segment 21 has a diameter larger than a diameter of the inner rear segment 22. A connection segment 24 is formed on a front end of the sleeve 20. A recycling groove is defined in an inner surface of the inner rear segment 22 and composed of a spiral groove 23 and a straight groove 25. The spiral groove 23 has a complete spiral pitch. A resilient limiting tab 26 is formed on a rear end of the sleeve 20 and has a rear end being a free end.

In the present embodiment, the sleeve has multiple engaging holes 241 defined in the connection segment 24 and two alignment protrusions 242 formed on the connection segment 24. The front end of the sleeve 20 is inserted into the space defined between the rear segment 14 and the connecting segment 16 of the connecting element 10. The second hooks 141 are selectively engaged with the engaging holes 241 in the sleeve 20. The alignment protrusions 242 are inserted respectively into the alignment notches 162.

The guiding tube 30 comprises a tubular body 31 and a front tube segment 32. The front tube segment 32 has an outer diameter smaller than an outer diameter of the tubular body 31 to define a shoulder 33 therebetween. The tubular body 31 has a tube hole 311 and a spiral guiding groove 34 defined in an inner surface of the tube hole 311. The guiding groove 34 has a complete spiral pitch. Multiple limiting ratchet tabs 35 are formed on an outer surface of the front tube segment 32, and a front tube hole 321 is defined in the front tube segment 32. Multiple holding notches 322 are defined in an inner surface of the front tube hole 321. A central hole 331 is defined in the guiding tube 30 at a position corresponding to the shoulder 33, and the front tube hole 321 communicates with the tube hole 311 via the central hole 331. The guiding tube 30 is mounted in the front segment 21 of the sleeve 20, and the front tube segment 32 extends out of the front end of the sleeve 20 and extends into the rear segment 14 of the connecting element 10. The limiting ratchet tabs 35 on the front tube segment 32 are engaged with the unidirectional teeth 12 in the rear segment 14 of the connecting element 10, such that the guiding tube 30 is limited to be rotated in a unidirectional manner. In addition, a locking tube 36 is formed around the central hole 331.

The screwing tube 40 has an axial hole 41 defined axially through the screwing tube 40. The screwing tube 40 has a guiding block 42, a guiding protrusion 43, a releasing channel 44, multiple annular grooves 45, and multiple unidirectional ratchet teeth 46. The guiding block 42 is formed on a front end of the screwing tube 40 and is moveably mounted in the guiding groove 34. The guiding protrusion 43 is formed on an outer surface at a middle portion of the screwing tube 40. The releasing channel 44 is longitudinally defined in the outer surface of the screwing tube 40 at the rear end of the screwing tube 40. The annular grooves 45 are defined around the outer surface of the screwing tube 40 and arranged longitudinally at evenly spaced intervals. The releasing channel 44 is diametrically opposite to the guiding protrusion 43. The unidirectional ratchet teeth 46 are faulted on an inner surface of the axial hole 41 near the rear end of the screwing tube 40. The guiding block 42 is mounted in the guiding groove 34. The rear end of the screwing tube 40 extends out of the rear end of the guiding tube 30 and the inner rear segment 22 of the sleeve 20. The guiding protrusion 43 is moveable in the recycling groove composed of the spiral groove 23 and the straight groove 25, such that the screwing tube 40 can be moved spirally along the spiral groove 23 or be moved forward and backward along the straight groove 25. The limiting tab 26 on the sleeve 20 can be shifted between the releasing channel 44 and the annular grooves 45. Preferably, the screwing tube 40 further has a pivotal connection portion 47 formed on the rear end of the screwing tube 40 and provided with hooks.

The screwing collar 50 is mounted in the front tube hole in the front tube segment 32 of the guiding tube 30. The screwing collar 50 has a threaded hole 51 defined in the screwing collar 50. Preferably, multiple holding blocks 52 are formed on an outer surface of the screwing collar 50 and are engaged respectively with the holding notches 322 in the front tube segment 32 of the guiding tube 30.

The pushing rod 60 is mounted in the screwing tube 40 and has a rod body 61 and a dose controlling segment 63. The rod body 61 has a non-circular cross section corresponding to the shape of the guiding hole 111 and an axial hole 62 having a non-circular cross section. The dose controlling segment 63 is formed on a front segment of the rod body 61 and provided with a thread 631. The thread 631 has a pitch smaller than a pitch of the spiral guiding groove 34. The dose controlling segment 63 has a non-circular cross section corresponding to the shape of the guiding hole 111. A flange is radially formed on and protrudes from a rear end of the dose controlling segment 63. An end flange is radially formed on a rear end of the rod body 61, and the rear end of the pushing rod 60 extends out of the screwing tube 40. The dose controlling segment 63 is screwed with the threaded hole 51 of the screwing collar 50 and extends through the guiding hole 111.

The front end of the pushing rod 60 can abut a piston 3A in the vial 3. Alternatively, a rod tube 65 is mounted securely on the front end of the rod body 61 to abut the piston 3A in the vial 3. The rod tube 65 has an abutting segment 651 and a holding segment 652 connected with the abutting segment 651. The holding segment 652 has multiple hooks 653 formed in the holding segment 652. The holding segment 652 is mounted around the front end of the rod body 61. The rod tube 65 is located in front of the inner flange 11 of the connecting element 10.

Preferably, multiple through holes 611 are defined radially in the pushing rod 60 and communicate with the axial hole 62. Multiple resilient hooks 612 are formed on the rod body 61, extend respectively into the through holes 611, and are selectively pushed by the locking tube 36 to extend into the axial hole 62. Multiple cavities are defined in an inner surface of the axial hole 62 at the rear end of the rod body 61. Multiple engaging holes 613 are radially defined in a front end of the dose controlling segment 63 and communicate with the axial hole 62.

The unidirectional ratchet collar 70 has a collar body 71 and multiple unidirectional ratchet tabs 72 formed on and protruding from an outer surface of the collar body 71. The collar body 71 has a through hole 711 defined through the collar body 71 and having a non-circular cross section corresponding to the shape of the axial hole 62 in the pushing rod 60. The ratchet collar 70 is mounted in the screwing tube 40 and is located behind the pushing rod 60. The unidirectional ratchet tabs 72 are engaged with the unidirectional ratchet teeth 46. Preferably, multiple collar hooks 73 are formed on a front end of the ratchet collar 70 and are engaged respectively with the cavities in the axial hole 62.

The injection device 80 comprises an injection rod 81 and an end cap 82 mounted moveably on a rear end of the injection rod 81. The injection rod 81 has a rod body 811 and a combining segment 812. The rod body 81 has a non-circular cross section corresponding to the shape of the axial hole 62. Multiple positioning recesses 813 are defined in the rod body 81. The combining segment 812 has a flange radially protruding from the combining segment 812. The rod body 811 of the injection rod 81 extends into the rear end of the sleeve 20 and the rear end of the screwing tube 40, through the through hole 711 of the ratchet collar 70, and into the axial hole 62 in the pushing rod 60. The collar hooks 73 are engaged respectively with the positioning recesses 813, such that the ratchet collar 70 is mounted securely on the rod body 811 of the injection rod 81. The end cap 82 is mounted in the rear end of the sleeve 20. The combining segment 812 and the pivotal connection portion 47 are mounted in the end cap 82, and the screwing tube 40 is rotatable relative to the end cap 82.

Preferably, multiple engaging faces 814 are formed on a front segment of the rod body 811 of the injection rod 81 and are selectively engaged with the resilient hooks 612. The end cap 82 has a cap body 821 and a lid 822. The cap body 821 has a combining hole. The combining segment 812 and the pivotal connection portion 47 are mounted through the combining hole in the cap body 821. The lid 822 is combined with a rear end of the cap body 821.

When in use, with reference to FIGS. 1 to 4, the vial housing 2 is applied to connect the vial 3, and the front end of the vial housing 2 is connected with a needle 4 that extends into the vial 3. The rear end of the vial housing 2 is connected with the front end of the connecting element 10. Preferably, the vial housing 2 has a connection segment 2A formed on the rear end of the vial housing 2. The connection segment 2A has multiple hook holes 2B. The connection segment 2A is mounted around the front segment 13 of the connecting element 10. The hook holes 2B are engaged respectively with the first hooks 131.

With reference to FIGS. 1 to 3, the syringe housing 6 is a hollow barrel, is mounted around the sleeve 20, and is connected with the rear end of the connecting element 10.

Figure 7:
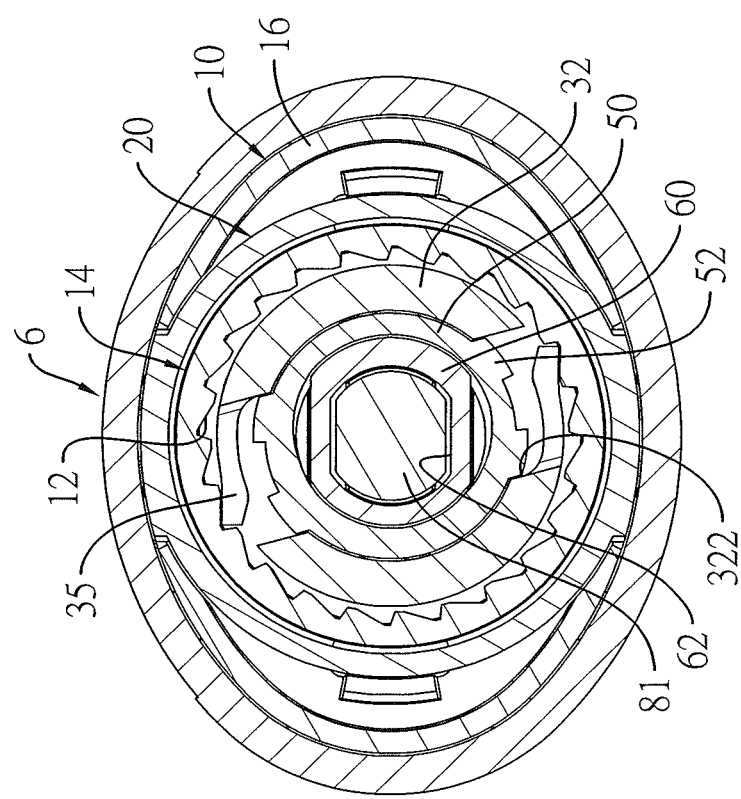
FIG. 7 is an enlarged cross sectional end view of the syringe along the line A-A in FIG. 4.

The combining segment 812 and the pivotal connection portion 47 extend out of the rear end of the syringe housing 6 and are combined with the end cap 82. Preferably, the front end of the syringe housing 6 is mounted around the connecting segment 16 and has multiple cavities 6A. The protrusions 161 on the connecting segment 16 are engaged respectively with the cavities 6A. With further reference to FIG. 7, the syringe cap 7 is mounted around the vial housing 2.

Figure 4:
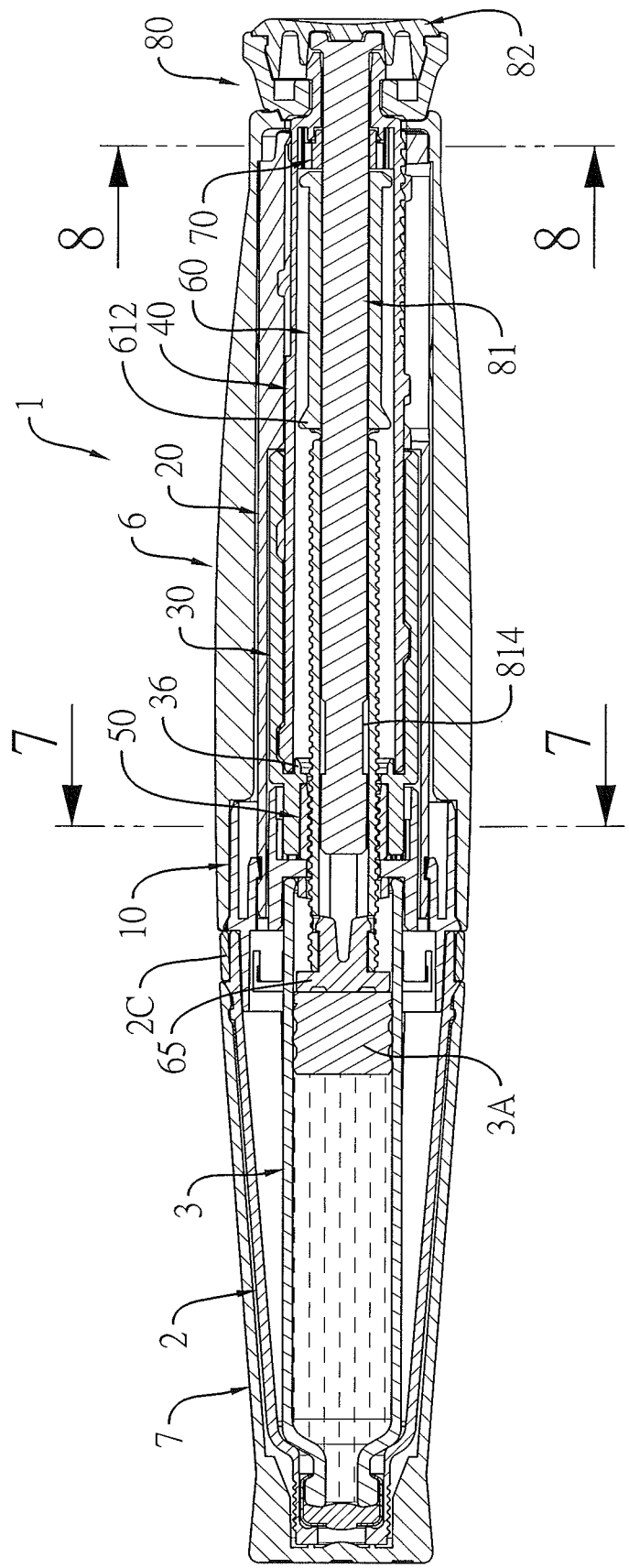
FIG. 4 is a cross sectional side view of the syringe in FIG. 1.
Figure 5:
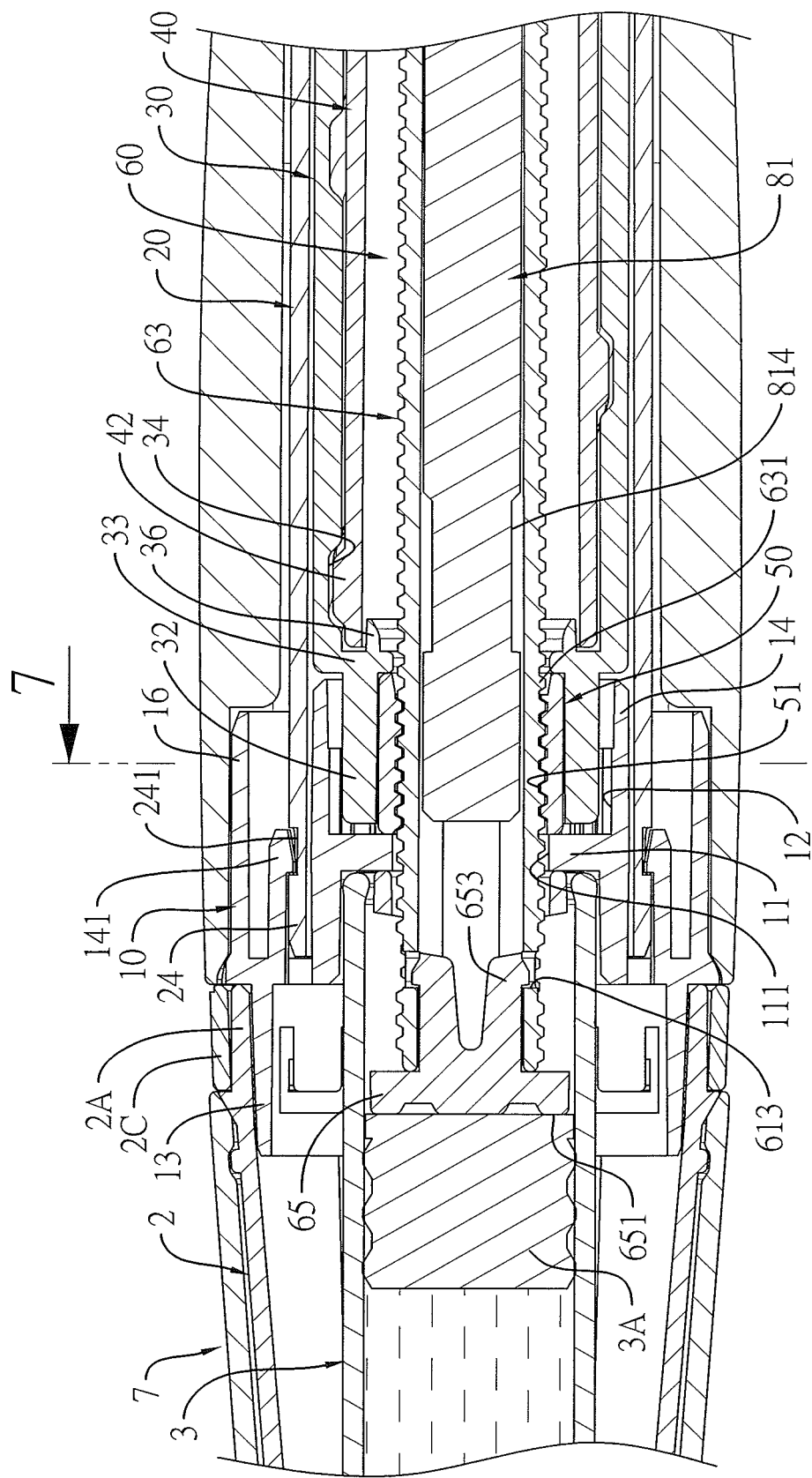
FIG. 5 is an enlarged cross sectional side view of the syringe in FIG. 1.
Figure 6:
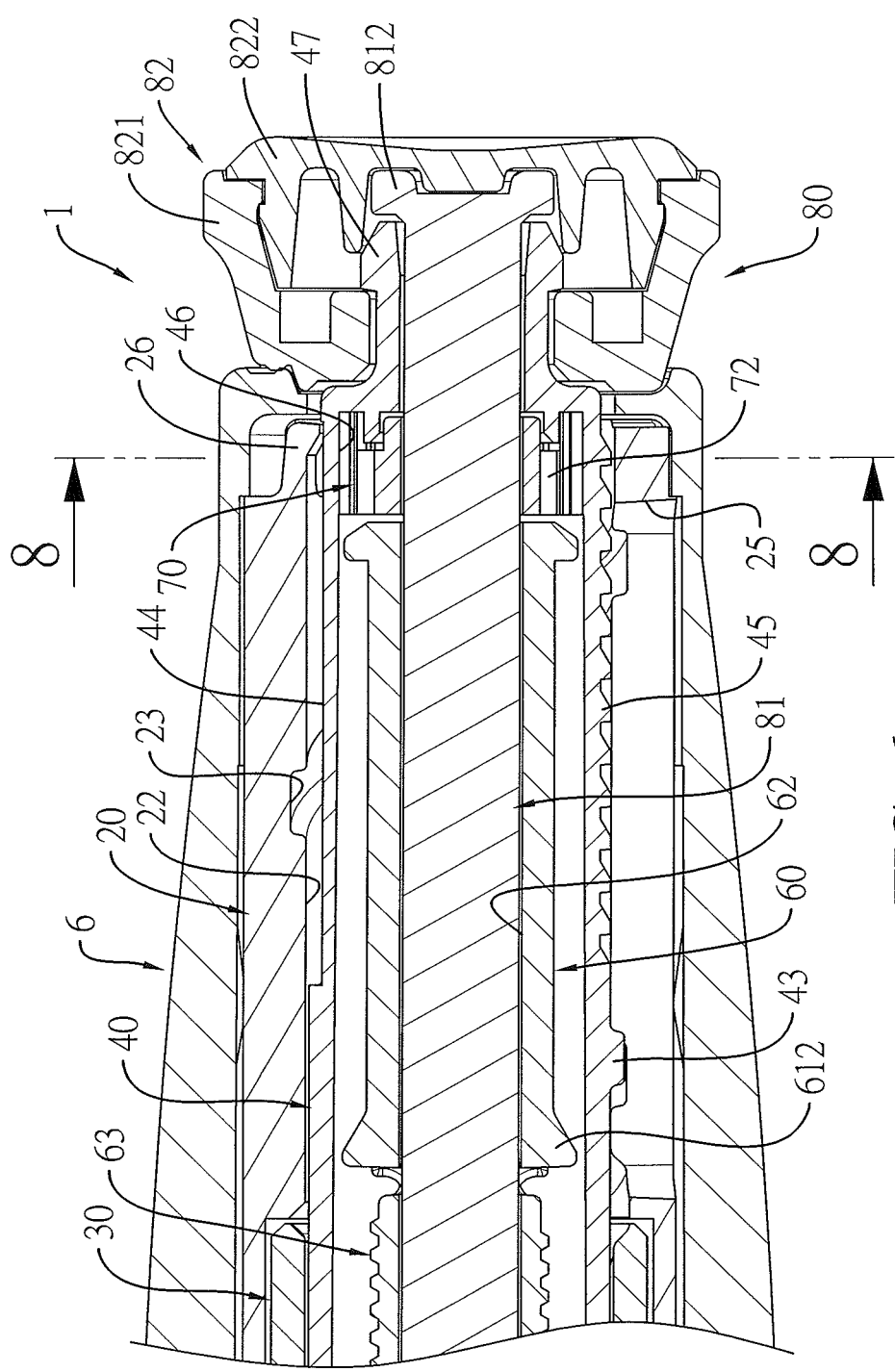
FIG. 6 is another enlarged cross sectional side view of the syringe in FIG. 1.
Figure 8:
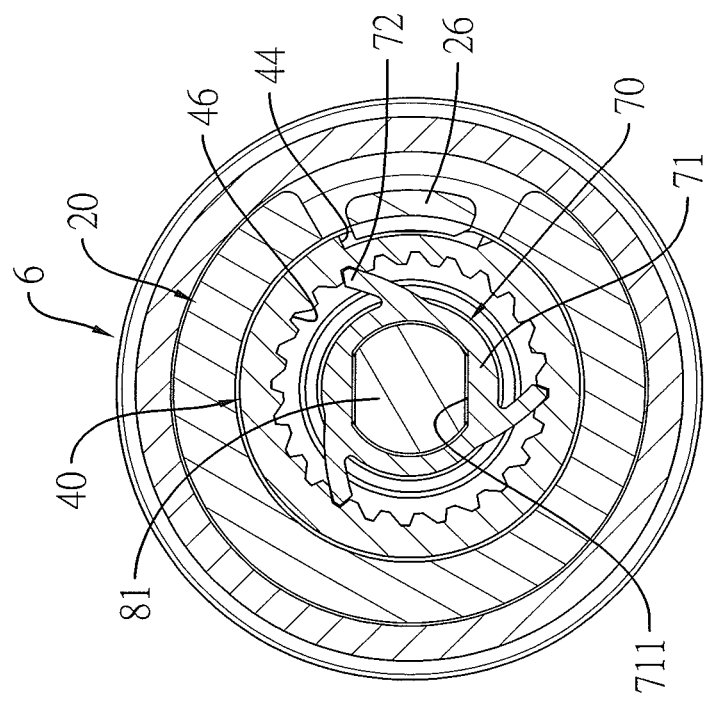
FIG. 8 is another cross sectional end view of the syringe along the line B-B in FIG. 4.

With reference to FIGS. 1, 4, and 5, the syringe is connected with the vial 3 before the vial housing 2 is connected with the injection assembly 1. The rear end of the vial 3 is inserted into the front segment 13 of the connecting element 10, and the rod tube 65 of the pushing rod 60 is inserted in the rear end of the vial 3 to abut the piston 3A. The vial housing 2 is then mounted around the vial 3, and the connecting segment 2A is mounted around the front segment 13 of the connecting element 10. At this time, the hook holes 2B are engaged respectively with the first hooks 131. In addition, the vial housing 2 may further have a securing collar 2C connected with the connection segment 2A, such that the vial housing 2 can be combined securely with the connecting element 10. Before the injection process, the syringe cap 7 is mounted around the vial housing 2.

With reference to FIGS. 4, 7, 8, and 11, to prepare the injection process, the syringe cap 7 is detached from the syringe and the needle 4 is attached to the front end of the vial housing 2 and extends into the vial 3. The needle cap 5 is mounted around the needle 4 to keep anyone from being stabbed by the needle 4. For injection, the injection device 80 is pulled backward to a preparation position.

Figure 9:
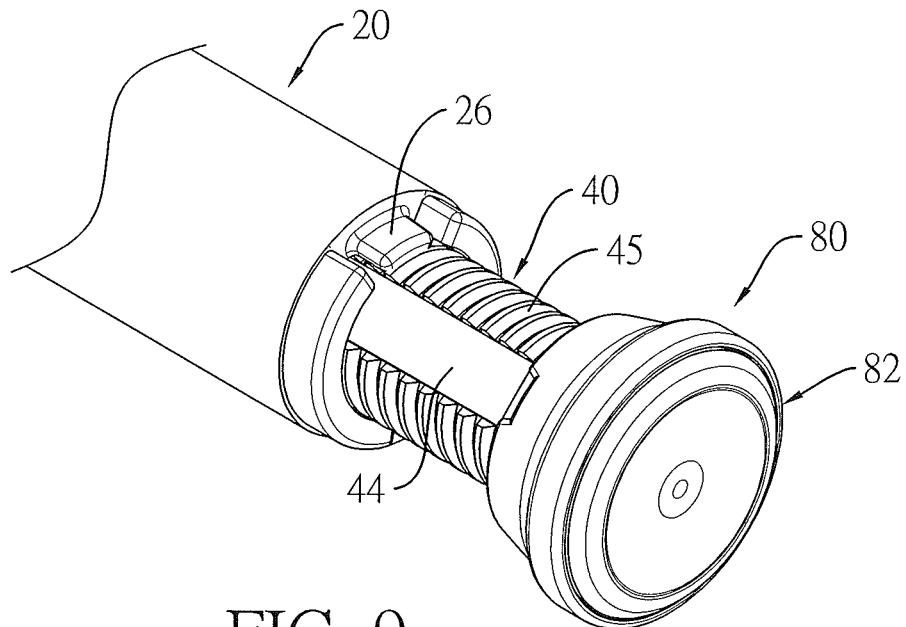
FIG. 9 is an enlarged partial perspective view of the syringe in FIG. 1.
Figure 10:
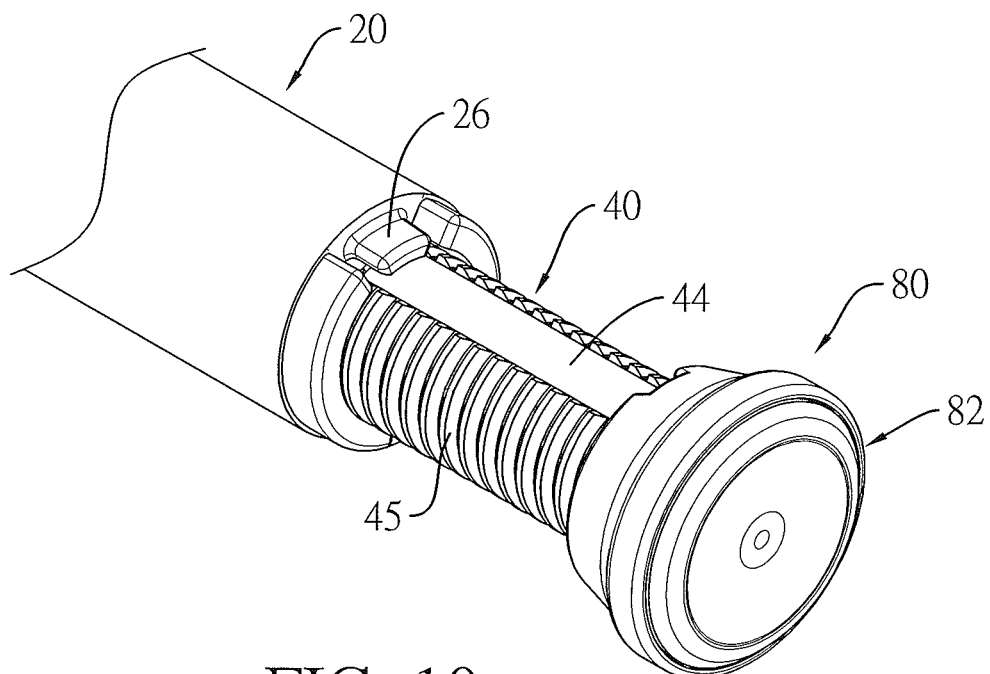
FIG. 10 is an enlarged operational partial perspective view of the syringe in FIG. 1.

When the injection device 80 is pulled backward, the screwing tube 40 will be moved backward. At this time, the screwing tube 40 is freely rotating relative to the sleeve 20 and the guiding tube 30, and the unidirectional ratchet tabs 72 on the ratchet collar 70 are engaged with the unidirectional ratchet teeth 46. The limiting ratchet tab 35 on the guiding tube 30 is engaged with the unidirectional teeth 12 in the connecting element 10. Consequently, the rotation direction of the injection rod 81 and the screwing tube 40 is limited, such that the screwing tube 40 can only be rotated in a unidirectional manner. With reference to FIG. 9, at this time, the liming tab 26 on the sleeve 20 moves over the annular groove 45 to generate sounds. With the engagement between the limiting tab 26 and one of the annular grooves 45, the injection device 80 can be prevented from being unintentionally pushed forward. Accordingly, the injection device 80 will not be pushed forward during the backward movement until the screwing tube 40 rotates a full circle. With reference to FIG. 10, when the limiting tab 26 moves into the releasing channel 44, the limiting tab 26 is unlocked.

Figure 11:
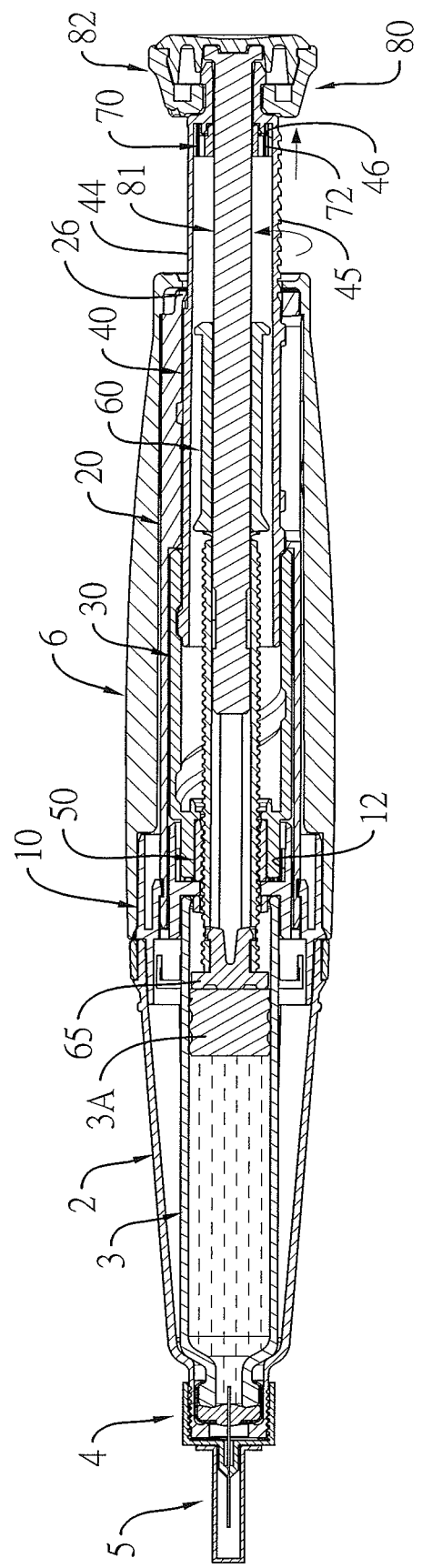
FIGS. 11 to 14 show operational cross sectional side views of the syringe in FIG. 1.
Figure 12:
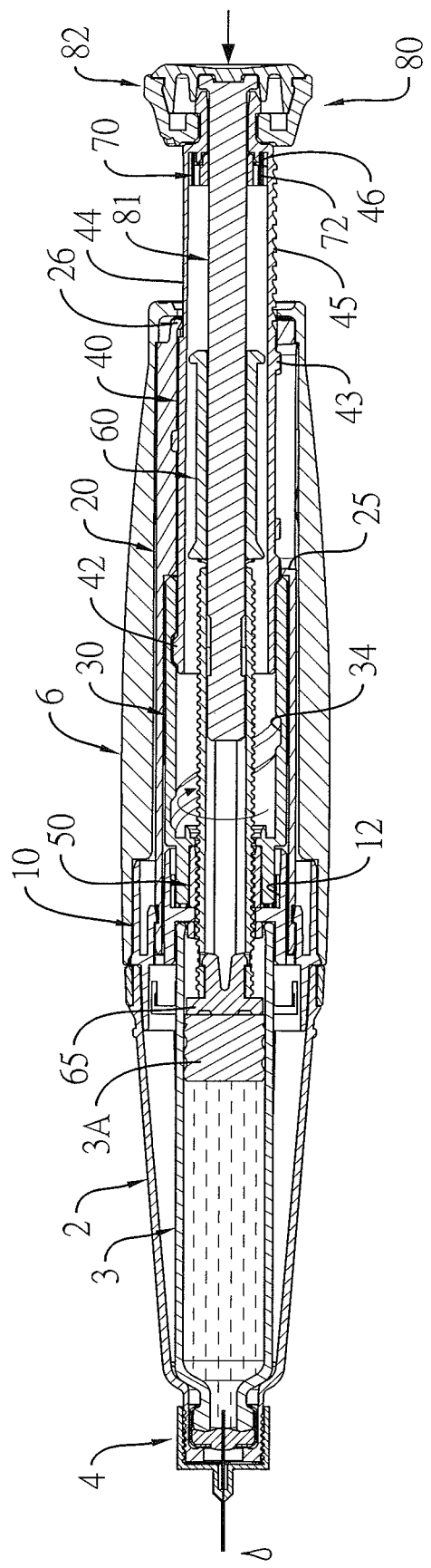
Figure 13:
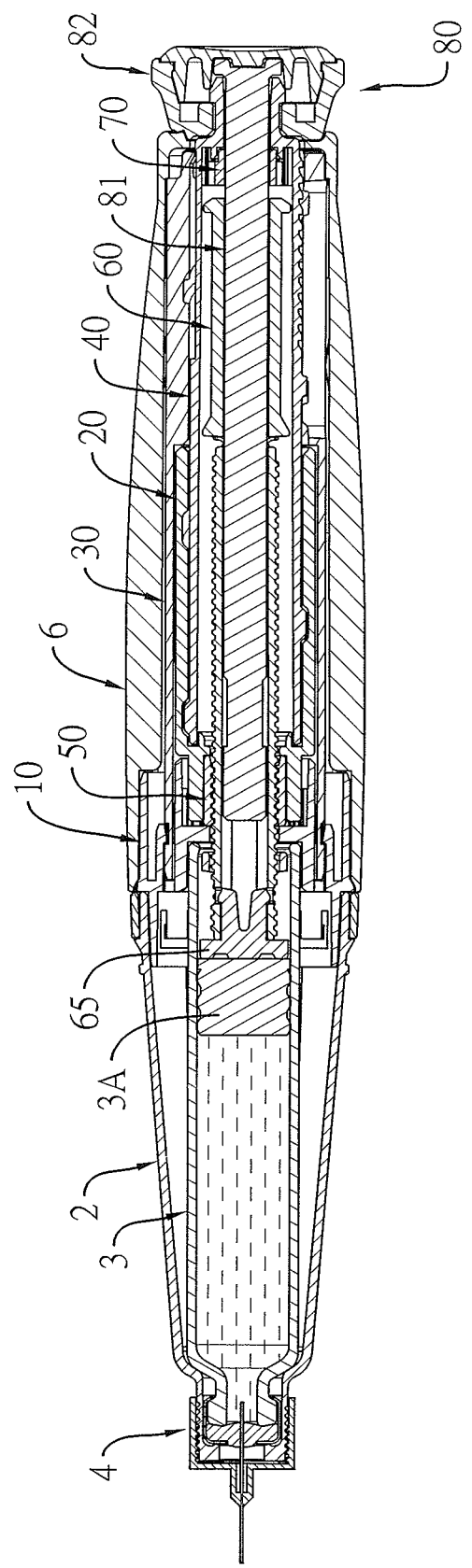

With reference to FIGS. 11 to 13, for injection, the needle cap 5 is detached from the syringe to pierce the needle into a human body. The injection device is pushed to inject medication into the human body. The injection device 80 is moved linearly when the end cap 82 is pushed forward, and the screwing tube 40 is simultaneously moved forward. During the movement, because the unidirectional ratchet tabs 72 on the ratchet collar 70 are engaged with the unidirectional ratchet teeth 46 in the screwing tube 40, the rotation direction of the injection rod 81 and the screwing tube 40 is limited. The pushing rod 60 is kept from rotating due to the non-circular guiding hole 11 in the connecting element 10. With further reference to FIG. 10, at this time, the limiting tab 26 is held in the releasing channel 44, and the guiding protrusion 43 is held in the straight groove 25. Thus, the screwing tube 40 can only be moved forward with the injection device 80. With the engagement between the guiding block 42 and the spiral guiding groove 34 in the guiding tube 30, the guiding tube 30 will be driven to rotate. After the screwing tube 40 is moved forward, the screwing tube 40 will not be moved backward again because of the arrangement of the spiral groove 23 and the guiding protrusion 43 of the screwing tube 40.

When the guiding block 42 on the screwing tube 40 is rotated for a full circle along the spiral guiding groove 34, the guiding tube 30 is also rotated for a full circle and the screwing collar 50 is also driven to rotate for a full circle. Consequently, the pushing rod 60 is driven to move forward for a predetermined distance to push the piston in the vial and to inject a predetermined dose of medication into the human body. Accordingly, the syringe has a dose metering function. At this time, because the pitch of the spiral guiding groove 34 is larger than that of the thread 631 on the pushing rod 60, the pushing force applied to the injection device 80 can be transformed to a rotating force. Accordingly, the rotating force along the large pitch along the spiral guiding groove 34 can be effectively transmitted to the small pitch along the thread 631, such that the syringe is labor-saving in operation.

Figure 14:
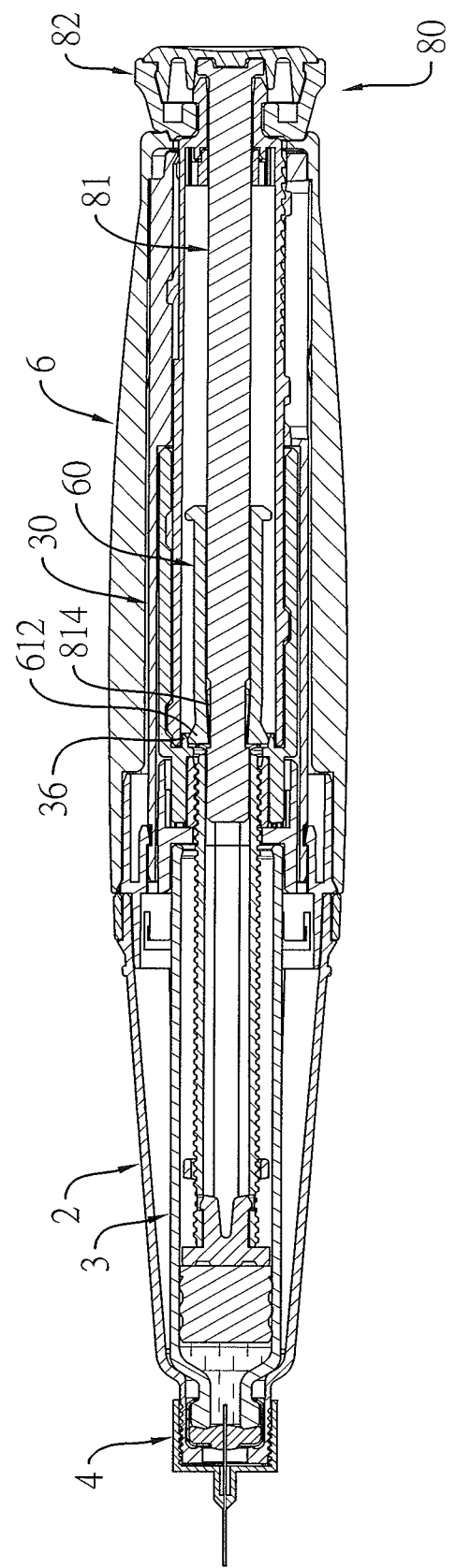
Figure 16:
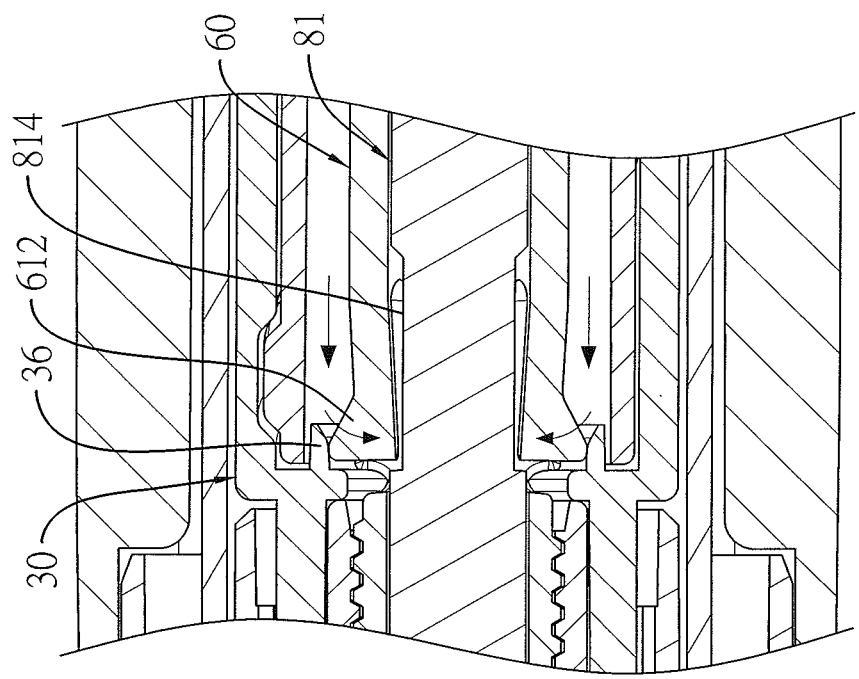
FIG. 16 is an enlarged operational cross sectional side view of the syringe in FIG. 1.
Figure 15:
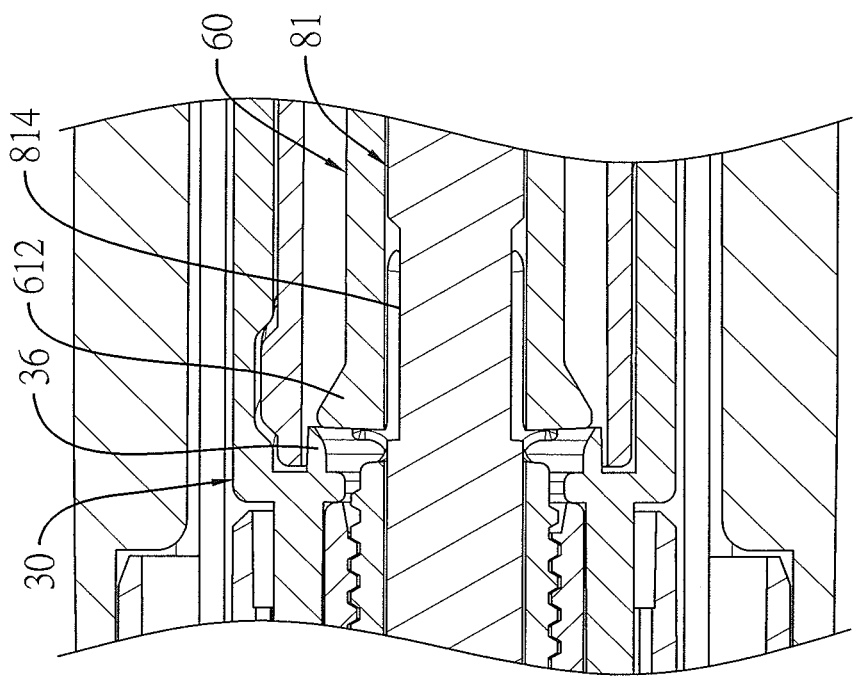
FIG. 15 is an enlarged operational cross sectional side view of the syringe in FIG. 1.

When the medication in the vial 3 is completely injected, with reference to FIGS. 14 to 16, the used syringe has to be discarded. When the pushing rod 60 is moved to a position where the resilient hooks 612 are pushed by the locking tube 36 in the guiding tube 30, the resilient hooks 612 will be bent and extend into the pushing rod 60 and will abut against the engaging faces 814 on the injection rod 81. With the engagement between the resilient hooks 612 and the engaging faces 814, the injection device 80 can be prevented from being pulled backward and is locked. Accordingly, the syringe can be kept from being repeatedly used and the safety of use of the syringe can be improved.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A syringe comprising
 an injection assembly comprising
  a connecting element having
   an inner flange formed in the connecting element and having a guiding hole defined through the inner flange; and
   multiple unidirectional teeth formed on an inner surface of the connecting element;
  a sleeve connected with a rear end of the connecting element and having
   an inner front segment;
   an inner rear segment communicating with the inner front segment;
   a recycling groove defined in an inner surface of the inner rear segment and composed of a spiral groove and a straight groove; and
   a resilient limiting tab formed on a rear end of the sleeve;
  a guiding tube mounted in the inner front segment of the sleeve and having
   a tubular body having a spiral guiding groove defined in an inner surface of the tubular body;

a front tube segment extending out of the inner front segment, extending into the rear end of the connecting element, and having
multiple limiting ratchet tabs formed on an outer surface of the front tube segment and engaged with the unidirectional teeth; and
a shoulder formed between the tubular body and the front tube segment,
a screwing tube mounted in the sleeve and the guiding tube, extending out of the rear ends of the sleeve and the guiding tube and having
an axial hole defined axially through the screwing tube;
a guiding block formed on a front end of the screwing tube and mounted in the spiral guiding groove;
a guiding protrusion formed on an outer surface of the screwing tube, at a middle portion of the screwing tube and being moveable in the recycling groove composed of the spiral groove and the straight groove;
a releasing channel longitudinally defined in the outer surface of the screwing tube and being diametrically opposite to the guiding protrusion;
multiple annular grooves defined around the outer surface of the screwing tube and arranged longitudinally at evenly spaced intervals, wherein the limiting tab on the sleeve is capable of being shifted between the releasing channel and the annular grooves; and
multiple unidirectional ratchet teeth formed on an inner surface of the axial hole;
a screwing collar mounted in the front tube segment of the guiding tube and having a threaded hole;
a pushing rod mounted in the screwing tube and having
a rod body having a non-circular cross section corresponding to a shape of the guiding hole of the connecting element; and
a dose controlling segment formed on a front segment of the rod body and provided with a thread that has a first pitch smaller than a second pitch of the spiral guiding groove, is screwed with the threaded hole in the screwing collar, and extends through the guiding hole in the connecting element;
a unidirectional ratchet collar mounted in the screwing tube, located behind the pushing rod, and having
a collar body; and
multiple unidirectional ratchet tabs formed on and protruding from an outer surface of the collar body and engaged with the unidirectional ratchet teeth of the screwing tube; and
an injection device having
an injection rod moveably extending into the sleeve and the screwing tube, through the ratchet collar, and into the axial hole in the pushing rod; and
an end cap mounted on a rear end of the injection rod and connected rotatably with a rear end of the screwing tube; and
a vial housing connected with the injection assembly.

2. The syringe as claimed in claim 1, wherein
the front tube segment of the guiding tube has an outer diameter smaller than an outer diameter of the tubular body;
the guiding tube has a tube hole defined in the guiding tube;
the spiral guiding groove is formed in an inner surface of the tube hole;
multiple limiting ratchet tabs are formed on an outer surface of the front tube segment;
a front tube hole is defined in the front tube segment;
a central hole is defined in the guiding tube at a position corresponding to the shoulder and the front tube hole communicates with the tube hole via the central hole;
multiple holding notches are defined in an inner surface of the front tube hole; and
the screwing collar has multiple holding blocks formed on an outer surface of the screwing collar and engaged respectively with the holding notches of the guiding tube.

3. The syringe as claimed in claim 1, wherein
the rod body of the pushing rod has multiple cavities defined in the inner surface of the axial hole at a rear end of the rod body;
the ratchet collar has multiple collar hooks formed on a front end of the ratchet collar and engaged respectively with the cavities in the axial hole of the rod body of the pushing rod;
the screwing tube further has a pivotal connection portion formed on the rear end of the screwing tube and provided with hooks;
the injection rod has a combining segment provided with a flange and formed on a rear end of the pushing rod;
the end cap comprises
a cap body having a combining hole; and
a lid mounted on a rear end of the cap body; and
the combining segment of the injection rod and the pivotal connection portion of the screwing tube are mounted through the combining hole in the cap body.

4. The syringe as claimed in claim 1, wherein the pushing rod has
multiple engaging holes radially defined in a front end of the dose controlling segment and communicating with the axial hole of the pushing rod; and
a rod tube mounted securely on a front end of the rod body of the pushing rod and having
an abutting segment; and
a holding segment connected with the abutting segment, mounted around the front end of the rod body of the pushing rod, and having multiple hooks formed in the holding segment and engaged respectively with the engaging holes in the rod body of the pushing rod.

5. The syringe as claimed in claim 1, wherein
the front tube segment of the guiding tube has an outer diameter smaller than an outer diameter of the tubular body of the guiding tube to define the shoulder between the tubular body and the front tube segment;
the guiding tube has a tube hole defined in the guiding tube;
the spiral guiding groove is formed in an inner surface of the tube hole;
multiple limiting ratchet tabs are foamed on an outer surface of the front tube segment;
a front tube hole is defined in the front tube segment;
a central hole is defined in the guiding tube at a position corresponding to the shoulder and the front tube hole communicates with the tube hole via the central hole;
multiple holding notches are defined in an inner surface of the front tube hole;
the screwing collar has multiple holding blocks formed on an outer surface of the screwing collar and engaged respectively with the holding notches of the guiding tube;

the rod body of the pushing rod has multiple cavities defined in an inner surface of the axial hole at a rear end of the rod body;
the ratchet collar has multiple collar hooks formed on a front end of the ratchet collar and engaged respectively with the cavities in the axial hole of the rod body of the pushing rod;
the screwing tube further has a pivotal connection portion formed on the rear end of the screwing tube and provided with hooks;
the injection rod has a combining segment provided with a flange and formed on the rear end of the pushing rod;
the end cap comprises
a cap body having a combining hole; and
a lid mounted on a rear end of the cap body;
the combining segment of the injection rod and the pivotal connection portion of the screwing tube are mounted through the combining hole in the cap body;
the pushing rod has
multiple engaging holes radially defined in a front end of the dose controlling segment and communicating with the axial hole of the pushing rod; and
a rod tube mounted securely on a front end of the rod body of the pushing rod and having
an abutting segment; and
a holding segment connected with the abutting segment, mounted around the front end of the rod body of the pushing rod, and having multiple hooks formed in the holding segment and engaged respectively with the engaging holes in the rod body of the pushing rod.

6. The syringe as claimed in claim 5, wherein
the injection rod has multiple engaging faces formed on a front segment of the injection rod;
the guiding tube has a locking tube in the guiding tube; and
the pushing rod has
multiple through holes defined radially in the pushing rod at a position adjacent to the dose controlling segment; and
multiple resilient hooks formed on the pushing rod, extending respectively into the through holes, and selectively pushed by the locking tube to each abut respectively against the engaging faces on the injection rod.

7. The syringe as claimed in claim 5 further comprising
a syringe housing being a hollow barrel, mounted around the sleeve, and connected with the rear end of the connecting element; and
a syringe cap mounted detachably around the vial housing, wherein
the combining segment of the injection rod and the pivotal connection portion of the screwing tube extend out of a rear end of the syringe housing and are combined with the end cap.

8. The syringe as claimed in claim 7, wherein
the connecting element comprises
a middle segment;
a front segment and a rear segment formed respectively at two ends of the middle segment; and
a connecting segment formed on and protruding from the middle segment, extending toward the rear segment, and disposed around the rear segment;
the rear segment has an outer diameter smaller than an outer diameter of the front segment;
multiple first hooks are formed on the front segment;
multiple protrusions are formed on and protrude from an outer surface of the connecting segment, and each protrusion has an inclined surface;
multiple second hooks are formed on a rear end of the middle segment and extend into a space defined between the connecting segment and the rear segment;
two alignment notches are defined in a rear end of the connecting segment;
the vial housing has a connection segment formed on a rear end of the vial housing, mounted around the front segment of the connecting element, and having multiple hook holes engaged respectively with the first hooks on the front segment of the connecting element;
the syringe housing has a front end mounted around the connecting segment of the connecting element and multiple cavities defined in the front end of the syringe housing and engaged respectively with the protrusions on the connecting segment of the connecting element;
the sleeve is inserted into the space defined between the rear segment and the connecting segment of the connecting element and has
multiple engaging holes defined in the connection segment of the sleeve and engaged respectively with the second hooks of the connecting element; and
two alignment protrusions inserted respectively into the alignment notches in the connecting segment of the connecting element.

9. The syringe as claimed in claim 8, wherein
the injection rod has multiple engaging faces formed on a front segment of the injection rod;
the guiding tube has a locking tube in the guiding tube; and
the pushing rod has
multiple through holes defined radially in the pushing rod at a position adjacent to the dose controlling segment; and
multiple resilient hooks formed on the pushing rod, extending respectively into the through holes, and selectively pushed by the locking tube to abut respectively against the engaging faces on the injection rod.

10. The syringe as claimed in claim 4, wherein
the injection rod has multiple engaging faces formed on a front segment of the injection rod;
the guiding tube has a locking tube in the guiding tube; and
the pushing rod has
multiple through holes defined radially in the pushing rod at a position adjacent to the dose controlling segment; and
multiple resilient hooks formed on the pushing rod, extending respectively into the through holes, and selectively pushed by the locking tube to abut respectively against the engaging faces on the injection rod.

11. The syringe as claimed in claim 3, wherein
the injection rod has multiple engaging faces formed on a front segment of the injection rod;
the guiding tube has a locking tube in the guiding tube; and
the pushing rod has
multiple through holes defined radially in the pushing rod at a position adjacent to the dose controlling segment; and
multiple resilient hooks formed on the pushing rod, extending respectively into the through holes, and selectively pushed by the locking tube to abut respectively against the engaging faces on the injection rod.

12. The syringe as claimed in claim 2, wherein
the injection rod has multiple engaging faces formed on a front segment of the injection rod;
the guiding tube has a locking tube in the guiding tube; and
the pushing rod has
   multiple through holes defined radially in the pushing rod at a position adjacent to the dose controlling segment; and
   multiple resilient hooks formed on the pushing rod, extending respectively into the through holes, and selectively pushed by the locking tube to abut respectively against the engaging faces on the injection rod.

13. The syringe as claimed in claim 1, wherein
the injection rod has multiple engaging faces formed on a front segment of the injection rod;
the guiding tube has a locking tube in the guiding tube; and
the pushing rod has
   multiple through holes defined radially in the pushing rod at a position adjacent to the dose controlling segment; and
   multiple resilient hooks formed on the pushing rod, extending respectively into the through holes, and selectively pushed by the locking tube to abut respectively against the engaging faces on the injection rod.

14. The syringe as claimed in claim 1 further comprising
a syringe housing being a hollow barrel, mounted around the sleeve, and connected with the rear end of the connecting element; and
a syringe cap mounted detachably around the vial housing, wherein
the combining segment of the injection rod and the pivotal connection portion of the screwing tube extend out of a rear end of the syringe housing and are combined with the end cap.

15. The syringe as claimed in claim 14, wherein
the connecting element comprises
   a middle segment;
   a front segment and a rear segment formed respectively at two ends of the middle segment; and
   a connecting segment formed on and protruding from the middle segment, extending toward the rear segment, and disposed around the rear segment;
the rear segment has an outer diameter smaller than an outer diameter of the front segment;
multiple first hooks are formed on the front segment;
multiple protrusions are formed on and protrude from an outer surface of the connecting segment, and each protrusion has an inclined surface;
multiple second hooks are formed on a rear end of the middle segment and extend into a space defined between the connecting segment and the rear segment;
two alignment notches are defined in a rear end of the connecting segment;
the vial housing has a connection segment formed on a rear end of the vial housing, mounted around the front segment of the connecting element, and having multiple hook holes engaged respectively with the first hooks on the front segment of the connecting element;
the syringe housing has a front end mounted around the connecting segment of the connecting element and multiple cavities defined in the front end of the syringe housing and engaged respectively with the protrusions on the connecting segment of the connecting element;
the sleeve is inserted into the space defined between the rear segment and the connecting segment of the connecting element and has multiple engaging holes defined in the connection segment of the sleeve and engaged respectively with the second hooks of the connecting element; and two alignment protrusions inserted respectively into the alignment notches in the connecting segment of the connecting element.

16. The syringe as claimed in claim 15, wherein the injection rod has multiple engaging faces formed on a front segment of the injection rod; the guiding tube has a locking tube in the guiding tube; and the pushing rod has multiple through holes defined radially in the pushing rod at a position adjacent to the dose controlling segment; and multiple resilient hooks formed on the pushing rod, extending respectively into the through holes, and selectively pushed by the locking tube to abut respectively against the engaging faces on the injection rod.

* * * * *